(12) United States Patent
Kohno et al.

(10) Patent No.: US 12,345,705 B2
(45) Date of Patent: Jul. 1, 2025

(54) IMMUNOCHROMATOGRAPHIC TEST STRIP AND IMMUNOCHROMATOGRAPHIC DETECTION KIT

(71) Applicant: SEKISUI MEDICAL CO., LTD., Tokyo (JP)

(72) Inventors: Keigo Kohno, Tokyo (JP); Kanako Itou, Tokyo (JP); Shun Sakai, Tokyo (JP); Akira Nakajima, Tokyo (JP); Motoki Morita, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 1056 days.

(21) Appl. No.: 17/294,183

(22) PCT Filed: Nov. 19, 2018

(86) PCT No.: PCT/JP2018/042627
§ 371 (c)(1),
(2) Date: May 14, 2021

(87) PCT Pub. No.: WO2020/105079
PCT Pub. Date: May 28, 2020

(65) Prior Publication Data
US 2022/0011306 A1    Jan. 13, 2022

(51) Int. Cl.
*G01N 33/543*  (2006.01)
*G01N 33/531*  (2006.01)
*G01N 33/553*  (2006.01)
*G01N 33/569*  (2006.01)

(52) U.S. Cl.
CPC ..... *G01N 33/54388* (2021.08); *G01N 33/531* (2013.01); *G01N 33/54306* (2013.01); *G01N 33/553* (2013.01); *G01N 33/56966* (2013.01)

(58) Field of Classification Search
CPC ........... G01N 33/531; G01N 33/54306; G01N 33/54386; G01N 33/54387; G01N 33/54388; G01N 33/553; G01N 33/56966; G01N 33/558
See application file for complete search history.

(56) References Cited

U.S. PATENT DOCUMENTS

| | | |
|---|---|---|
| 6,270,637 B1 | 8/2001 | Crismore et al. |
| 10,422,798 B2 | 9/2019 | Kohno et al. |
| 2002/0036170 A1 | 3/2002 | Harvey et al. |
| 2012/0015429 A1* | 1/2012 | Zhou ............... G01N 33/54388 422/68.1 |
| 2016/0274100 A1* | 9/2016 | Kobayashi ....... G01N 33/54388 |
| 2017/0370926 A1 | 12/2017 | Kohno et al. |
| 2020/0081002 A1 | 3/2020 | Kohno et al. |

FOREIGN PATENT DOCUMENTS

| | | |
|---|---|---|
| CN | 101893627 A | 11/2010 |
| CN | 107209179 A | 9/2017 |
| CN | 107966561 A | 4/2018 |
| EP | 2 418 488 A1 | 2/2012 |
| EP | 3 236 261 B1 | 9/2020 |
| JP | 2015-072181 A | 4/2015 |
| JP | 2015-72181 A | 4/2015 |
| JP | 2016-28241 A | 2/2016 |
| JP | 2016-176938 A | 10/2016 |
| JP | 2018-048818 A | 3/2018 |
| JP | 2018-48818 A | 3/2018 |
| JP | 6426872 B1 | 11/2018 |
| WO | WO 03/014726 A1 | 2/2003 |
| WO | WO 2010/116979 A1 | 10/2010 |
| WO | WO 2011/125606 A1 | 10/2011 |
| WO | WO 2018/030365 A1 | 2/2018 |

OTHER PUBLICATIONS

Meisei (ALKOX. Meisei Chemical Works, Ltd. Product Information. wwwdotmeisei-chemdotcodotjp—(Oct. 31, 2024)).*
Extended European Search Report for European Application No. 18940974.1, dated Jun. 9, 2022.
International Preliminary Report on Patentability and English translation of the Written Opinion of the International Searching Authority (Forms PCT/IB/338, PCT/IB/373, and PCT/ISA/237) for International Application No. PCT/JP2018/042627, dated Jun. 3, 2021.
Chinese Office Action and Search Report for Chinese Application No. 201880099528.5, dated Feb. 23, 2024, with an English translation.
Office Action for corresponding European Application No. 18940974.1, dated Feb. 20, 2023.
Alkox® L Series, Meisei Chemical Works, Ltd., Aug. 9, 2016, total 8 pages.
International Search Report for PCT/JP2018/042627 mailed on Feb. 5, 2019.
Office Action for JP 2018-146308 dated Aug. 10, 2018.
Written Opinion of the International Searching Authority for PCT/JP2018/042627 (PCT/ISA/237) mailed on Feb. 5, 2019.

* cited by examiner

*Primary Examiner* — Gailene Gabel
(74) *Attorney, Agent, or Firm* — Birch, Stewart, Kolasch & Birch, LLP

(57) ABSTRACT

An immunochromatographic test strip that enables a specimen to sufficiently and quickly permeate into a sample application region within a test time, reducing variations in detection values of a test line. The test strip maintains consistent detection values even with whole blood specimens. The immunochromatographic test strip includes at least a sample application region, a development region, and a detection region, wherein the sample application region contains polyethylene glycol having a molecular weight of 15,000 to 700,000.

15 Claims, 3 Drawing Sheets

IMMUNOCHROMATOGRAPHIC TEST STRIP AND IMMUNOCHROMATOGRAPHIC DETECTION KIT

TECHNICAL FIELD

The present invention relates to a test strip for immunochromatography and an immunochromatographic detection kit including the test strip. The present invention relates to more specifically a test strip for immunochromatography having a sample application region treated with a specific polymer, and an immunochromatographic detection kit including the test strip.

BACKGROUND ART

As use of POCT (point of care testing) for treatment near patients becomes widespread, a lateral flow immunochromatographic detection method using a test strip of nitrocellulose membrane etc. becomes widely used as a simple immunoassay using antigen-specific binding substance reaction.

An immunochromatography based test strip (hereinafter referred to as an immunochromatographic test strip) generally consists of a sample application region, a development region, and a detection region located on a porous membrane. A labeled specific binding substance forming a complex with an analyte is held in a development start site of the development region so as to be able to travel down the development region and reach the detection region, by dissolving upon contact with a specimen (sample). The immobilized specific binding substance is immobilized in a certain spot on the development region on the downstream side to constitute the detection region. When the specimen is dropped onto the sample application region, and the specimen includes an analyte, the analyte in the specimen specifically binds to the labeled specific binding substance to form a complex. The complex is developed in the development region in the downstream direction and further binds to the immobilized specific binding substance. Therefore, the analyte can qualitatively or quantitatively be analyzed by detecting a sandwich type complex of the labeled specific binding substance, the analyte, and the immobilized specific binding substance in a specific binding substance-immobilized portion. An example of a label constituting a detection reagent (conjugate) such as a labeled specific binding substance is colloidal gold particles, and qualitative detection is enabled by a color reaction due to the colloidal gold particles. Furthermore, the analyte in the specimen can quantitatively be detected based on a degree of color development.

Since the sample application region such as a sample pad of the conventional immunochromatographic test strip is not provided with sufficient hydrophilicity, the specimen may not sufficiently permeate the sample pad within a predetermined test time. Therefore, a degree of color development on a test line may vary depending on the degree of permeation. Particularly, when the specimen is whole blood, the degree of permeation into the sample pad significantly varies, which hinders accurate measurement.

In a specimen analysis tool disclosed in Patent Document 1, to prevent a reduction in permeability of a developing solution in a developing solution supply region due to a hydrophobic component eluted from a plastic base material in which the immunochromatographic test strip is stored, a surface of the developing solution supply region is provided with a hydrophilic component layer made of saccharide, a surfactant, etc. However, no studies were conducted on variations in the sample application and the case where no hydrophobic component is eluted from the plastic base material, and only sucrose, N-methylglucose amine, SDS, and PVP were specifically tested in the examples.

CITATION LIST

Patent Literature

Patent Document 1: WO 2010/116979

SUMMARY OF INVENTION

Technical Problem

A problem to be solved by the present invention is to provide an immunochromatographic test strip in which a specimen applied to a sample application region sufficiently permeates the immunochromatographic test strip within a test time so that variations in detection values on a test line can be prevented. Particularly, a problem to be solved by the present invention is to provide an immunochromatographic test strip causing less variations in detection values even when the specimen is whole blood.

Solution to Problem

The present invention is for the purpose of solving the problem, and we found that by containing polyethylene glycol (hereinafter also referred to as PEG) having a certain molecular weight in a sample application region of an immunochromatographic test strip, a specimen is allowed to quickly permeate the test strip in the sample application region, so that variations in detection values can be prevented, thereby completing the present invention. Specifically, the present invention has the following configurations.

(1) An immunochromatographic test strip comprising at least a sample application region, a development region, and a detection region, wherein the sample application region contains polyethylene glycol having a molecular weight of 15,000 to 700,000.

(2) The immunochromatographic test strip according to (1), wherein the immunochromatographic test strip comprises a sample pad as the sample application region.

(3) The immunochromatographic test strip according to (1) or (2), wherein a specimen applied to the sample application region is plasma or whole blood.

(4) The immunochromatographic test strip according to any one of (1) to (3), wherein a specimen applied to the sample application region is whole blood.

(5) The immunochromatographic test strip according to any one of (1) to (4), wherein a specific binding substance binding to an analyte and labeled with colloidal gold is held in a dissolvable state in the development region.

(6) The immunochromatographic test strip according to (5), wherein the immunochromatographic test strip comprises a conjugate pad in which the specific binding substance binding to the analyte and labeled with colloidal gold is held in a dissolvable state.

(7) The immunochromatographic test strip according to any one of (2) to (6), wherein a 3rd Pad for blood cell separation is placed between the sample pad and the detection region.

(8) The immunochromatographic test strip according to any one of (1) to (7), wherein the sample application region further contains an erythrocyte agglutinating agent or an erythrocyte binding component.

(9) The immunochromatographic test strip according to (8), wherein the erythrocyte agglutinating agent is polybrene.

(10) The immunochromatographic test strip according to any one of (1) to (9), wherein the content of the polyethylene glycol per area of the sample application region is 0.00630 to 0.473 mg/cm$^2$.

(11) An immunochromatographic test strip comprising at least:
(a) a sample pad containing polyethylene glycol having a molecular weight of 15,000 to 700,000;
(b) a conjugate pad in which a specific binding substance binding to an analyte and labeled with colloidal gold is held in a dissolvable state; and
(c) a membrane on which a specific binding substance binding to an analyte is immobilized.

(12) The immunochromatographic test strip according to (11), wherein a 3rd Pad for blood cell separation is placed between the sample pad and the membrane.

(13) The immunochromatographic test strip according to (11) or (12), wherein the sample pad is made of glass fiber.

(14) The immunochromatographic test strip according to any one of (11) to (13), wherein the conjugate pad is made of glass fiber.

(15) An immunochromatographic detection kit comprising: the immunochromatographic test strip according to any one of (11) to (14).

(16) A method for producing an immunochromatographic test strip comprising at least a sample application region, a development region, and a detection region, the method comprising:
impregnating the sample application region with a solution containing polyethylene glycol having a molecular weight of 15,000 to 700,000, and drying the sample application region.

(17) The method for producing an immunochromatographic test strip according to (16), wherein the immunochromatographic test strip comprises a sample pad as the sample application region.

(18) The method for producing an immunochromatographic test strip according to (17), wherein the solution containing polyethylene glycol having a molecular weight of 15,000 to 700,000 is a solution having a concentration of the polyethylene glycol adjusted so that a retaining amount of the polyethylene glycol per area of the sample pad is 0.00630 to 0.473 mg/cm$^2$.

(19) An immunochromatographic test method using the immunochromatographic test strip according to any one of (1) to (14), the immunochromatographic detection kit according to (15), or the immunochromatographic test strip produced by the method according to any one of (16) to (18), the method comprising:
dropping the specimen onto the sample application region of the immunochromatographic test strip, and
detecting color development of the detection region of the immunochromatographic test strip after a predetermined time.

The present invention further includes the following aspects.

(A-1) A method for suppressing variations in measurement values by using the following immunochromatographic test strip in an immunochromatographic detection method for detecting an analyte in a specimen:
an immunochromatographic test strip comprising at least a sample application region, a development region, and a detection region, wherein the sample application region contains polyethylene glycol having a molecular weight of 15,000 to 700,000.

(A-2) The method according to (A-1), wherein the immunochromatographic test strip includes a sample pad serving as the sample application region.

(A-3) The method according to (A-1) or (A-2), wherein a specimen applied to the sample application region is plasma or whole blood.

(A-4) The method according to any one of (A-1) to (A-3), wherein a specimen applied to the sample application region is whole blood.

(A-5) The method according to any one of (A-1) to (A-4), wherein a specific binding substance binding to an analyte and labeled with colloidal gold is held in a dissolvable state in the development region.

(A-6) The method according to (A-5), wherein the immunochromatographic test strip includes a conjugate pad in which a specific binding substance binding to an analyte and labeled with colloidal gold is held in a dissolvable state.

(A-7) The method according to (A-6), wherein a 3rd Pad for blood cell separation is placed between the sample pad and the detection region.

(A-8) The method according to any one of (A-1) to (A-7), wherein the sample application region further contains an erythrocyte agglutinating agent or an erythrocyte binding component.

(A-9) The method according to (A-8), wherein the erythrocyte agglutinating agent is polybrene.

(A-10) The method according to any one of (A-1) to (A-9), wherein the content of the polyethylene glycol per area of the sample application region is 0.00630 to 0.473 mg/cm$^2$.

(B-1) A method for suppressing variations in measurement values by using an immunochromatographic test strip including at least the following (a) to (c) in an immunochromatographic detection method for detecting an analyte in a specimen:
(a) a sample pad containing polyethylene glycol having a molecular weight of 15,000 to 700,000;
(b) a conjugate pad in which a specific binding substance binding to an analyte and labeled with colloidal gold is held in a dissolvable state; and
(c) a membrane on which a specific binding substance binding to an analyte is immobilized.

(B-2) The method according to (B-1), wherein a 3rd Pad for blood cell separation is placed between the sample pad and the membrane.

(B-3) The method according to (B-1) or (B-2), wherein the sample pad is made of glass fiber.

(B-4) The method according to any one of (B-1) to (B-3), wherein the conjugate pad is made of glass fiber.

(C-1) An immunochromatographic test strip comprising at least a sample application region, a development region, and a detection region, wherein the sample application region contains polyethylene glycol having a molecular weight of 15,000 to 700,000, and wherein an analyte is selected from the groups consisting of inflammation-related markers, coagulation or fibrinolysis markers such as fibrin degradation products, soluble fibrin, TAT (thrombin-antithrombin complex), and PIC (plasmin-plasmin inhibitor complex), circulation-related markers such as oxidized LDL, BNP (brain natriuretic peptide), H-FABP (cardiac fatty acid-binding protein), and cardiac troponin I (cTnI), metabolism-related markers such as adiponectin, tumor markers such as CEA (carcinoembryonic antigen), AFP (α-fetoprotein), CA19-9, CA125, and PSA (prostate-specific antigen), infectious disease-related markers such as HBV (hepatitis B virus), HCV (hepatitis C virus), *Chlamydia trachomatis*, and gonococcus, allergen-specific IgE (immunoglobulin E), hormones, and drugs.

(D) An immunochromatographic test method using the following test strip, the method comprising the steps of:
dropping a specimen onto a sample application region of the test strip;
reacting an analyte in the sample with a specific binding substance of an immunochromatographic test strip for a predetermined time; and
optically detecting color development in a detection region of the immunochromatographic test strip, wherein
the test strip is an immunochromatographic test strip comprising at least the sample application region, a development region, and the detection region, wherein the sample application region contains polyethylene glycol having a molecular weight of 15,000 to 700,000.

Advantageous Effects of Invention

According to the present invention, by containing polyethylene glycol having a certain molecular weight in the sample application region of the immunochromatographic test strip, the specimen is allowed to quickly permeate into the sample application region of the test strip, so that variations in detection values can be prevented. Furthermore, since the specimen quickly permeates into in the sample application region of the test strip, the detection region reliably develops color within a predetermined reaction time, and an examination can be prevented from being delayed due to unsuccessful examination or re-examination. Particularly, even if the specimen is whole blood, rapid penetration of the specimen into the test strip can be achieved, and variations in detection value can significantly be suppressed.

DESCRIPTION OF EMBODIMENTS (Immunochromatographic Test Strip)

Figure 1:
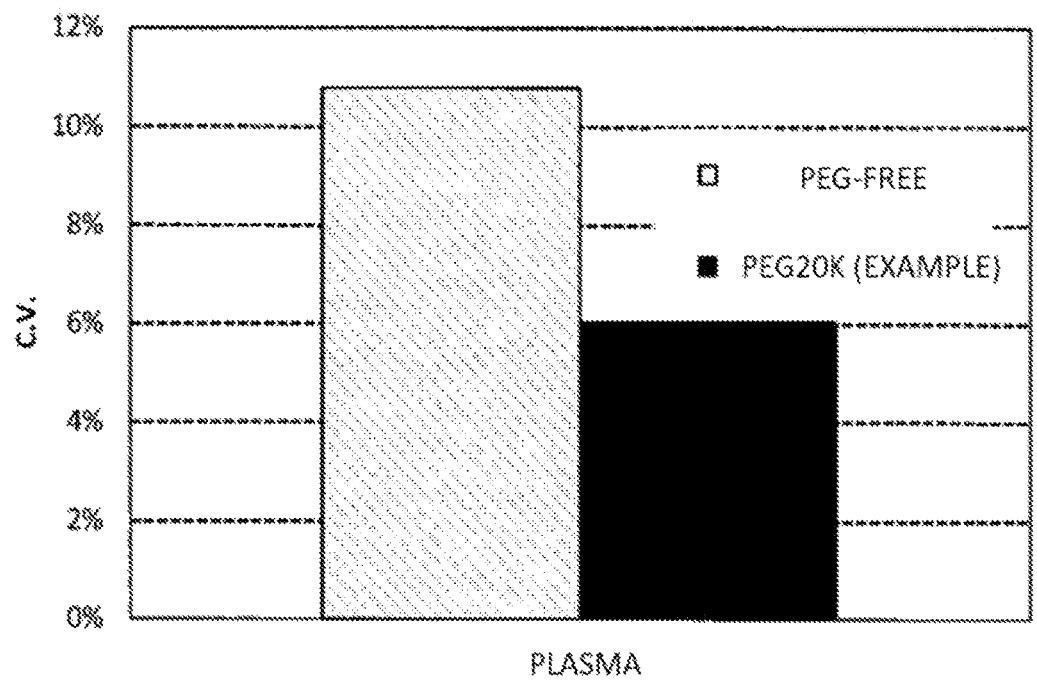
FIG. 1 is a graph showing a variation (C.V.) in measurement value when a specimen is plasma in the cases of sample pads containing PEG (the present invention) and not containing PEG (Comparative Example).

An immunochromatographic test strip of the present invention includes a porous membrane equipped with at least a "sample application region", a "development region", and a "detection region". A labeled specific binding substance forming a complex with an analyte is held in a development region so as to be able to travel down the development region and reach the detection region, by dissolving upon contact with a specimen. A specific binding substance for detection is further immobilized on a portion of the development region to constitute the detection region.

An example of a test strip embodying these elements is a test strip including a sample pad serving as the sample application region, a conjugate pad in which a labeled specific binding substance that binds to an analyte is retained in a dissolvable state and is serving as a portion of the development region, and a porous membrane having a portion on which a specific binding substance for detection is immobilized and serving as the development region and the detection region. Specifically, a typical immunochromatographic test strip of the present invention has the following configuration:

(1) sample pad to which a specimen is applied;
(2) a conjugate pad placed in contact between the sample pad and the membrane comprising the development region and retaining a conjugate sensitized with a first specific binding substance on a colloidal gold surface in a dissolvable state; and
(3) a porous membrane placed in contact with the conjugate pad and having a second specific binding substance immobilized on the downstream side in the development direction that binds to a complex of a conjugate and an analyte.

The sample pad, the conjugate pad, and the porous membrane may each constitute a separate carrier, or two of them may constitute one carrier, and any form may be available as long as the sample pad, the conjugate pad, and the porous membrane are placed in this order from upstream to downstream in the development direction so that a liquid containing a specimen is developed.

In addition to the constituent elements described above, the immunochromatographic test strip may have one or more of absorption pads and 3rd pads further placed and mounted thereon. The test strip can usually be arranged on a solid phase support such as a plastic adhesive sheet. A polyester film etc., may be laminated on a surface of the test strip for the purpose of increasing the mechanical strength of the porous membrane on which the specific binding substance is immobilized and preventing evaporation of moisture (drying) during an assay.

A method for detecting an analyte in a specimen by using the immunochromatographic test strip of the present invention has at least the following steps:

dropping the specimen to the sample application region; bringing the analyte in the specimen into contact with a conjugate to form a complex; and detecting the complex of the analyte in the specimen and the conjugate in the detection region.

Since the sample application region of the immunochromatographic test strip of the present invention is pretreated with certain PEG, the specimen can quickly permeate from the sample application region and move to the development region. Therefore, the reaction can be allowed to progress to a certain extent within a predetermined time so as to suppress variations in detection values.

(Pretreatment of Sample Application Region with PEG)

In the present invention, the sample application region is characterized by being pretreated with polyethylene glycol (hereinafter also referred to as PEG) having a molecular weight of 15,000 to 700,000. Pretreatment refers to inclusion of the PEG in the sample application region and includes either retention or supporting in a dissolvable state or non-elutable immobilization. Containing PEG having a certain molecular weight provides effects of allowing a specimen (also referred to and having the same meaning as a sample) to quickly permeate the test strip and improving variations in measurement values.

This is because if the molecular weight is less than 15,000, the ability to allow the specimen to permeate the test strip is poor, and if the molecular weight is greater than 700,000, the water solubility of PEG itself becomes low, which makes the ability to allow the specimen to permeate the test strip poor, so that a variation in development cannot be suppressed. The molecular weight of PEG of the present invention is more preferably 15,000 to 500,000, further preferably 15,000 to 100,000.

The molecular weight of PEG in the present invention refers to a number average molecular weight unless otherwise specified. The number average molecular weight can be measured and calculated by a hydroxyl value analysis, and the hydroxyl value can be measured by an acetic anhydride/pyridine method.

Examples of commercially available products of polyethylene glycol having a number average molecular weight of 15,000 to 700,000 of the present invention include PEG 20,000 (average molecular weight: 18,000 to 25,000, Kishida Chemical Co., Ltd.) and PEG 70,000 (FUJIFILM Wako Pure Chemical Corporation), PEG 500,000 (average molecular weight: 300,000 to 500,000, FUJIFILM Wako Pure Chemical Corporation), etc. Other examples of commercially available polyethylene glycol products include ADEKA PEG (ADEKA) and PEG (Sanyo Chemical Industries, Ltd.). Hereinafter, PEG 20,000, PEG 70,000, and PEG 500,000 may be referred to as PEG20K, PEG70K, and PEG500K, respectively.

In the present invention, when the test strip has a sample pad, PEG needs to be contained in at least the sample application region of the sample pad. PEG may be contained in the entire sample pad.

When the sample application region is included on the same insoluble membrane without the sample pad, the PEG of the present invention needs to be contained in at least the sample application region of the insoluble membrane. The PEG may be contained not only in the sample application region but also on the downstream side thereof.

Examples of a method of containing PEG in the sample pad include a method of applying a solution containing PEG to the sample pad etc., and a method of impregnating the sample pad with these solutions and drying the sample pad to contain PEG on the surface or inside of the sample pad.

The certain PEG of the present invention is retained at preferably 0.00630 to 0.473 mg/cm$^2$ per area of the sample application region.

This is because in the case of less than 0.00630 mg/cm$^2$, the ability to allow the specimen to permeate the test strip is poor, and in the case of more than 0.473 mg/cm$^2$, unnecessary interaction with a detection reagent occurs, resulting in excessive aggregation of the conjugate or a blank reaction in the detection region. The retaining amount of PEG is more preferably 0.0630 to 0.473 mg/cm$^2$, further more preferably 0.0630 to 0.315 mg/cm$^2$, and most preferably 0.0945 to 0.189 mg/cm$^2$.

In a method of applying the PEG having a certain molecular weight of the present invention is as follows: preparing a solution containing PEG at a predetermined concentration, applying the solution to a sample pad or an insoluble membrane carrier in a line shape etc. by using an apparatus etc. having a mechanism capable of moving a nozzle in a horizontal direction while discharging the solution at a constant rate therefrom, and drying, so that the PEG is contained in a dissolvable state. Alternatively, a certain amount of a PEG solution having a predetermined concentration may be collected with a pipette etc. and applied to a portion or the entire surface of the sample pad. When the PEG is applied to the entire surface, the sample pad can be immersed in a container containing a PEG solution having a predetermined concentration so that the PEG is applied to the entire surface.

The concentration of the PEG solution may be adjusted such that the preferable retaining amount described above is achieved, and when it is assumed that the area of the standard sample application region is 0.96 cm$^2$ and an application amount is 60.5 μL, C is 0.01% to 0.75% from the following equation. C is more preferably 0.1 to 0.75%, further preferably 0.1 to 0.5%, most preferably 0.15 to 0.3%.

$$A(mg/cm^2)=B\ \mu L \times (C\%/100)/D\ cm^2$$

A: amount of PEG held per unit area of the sample application region

B: amount of PEG-containing solution allowed to permeate the sample application region C: % concentration (w/v) of PEG in PEG-containing solution D: area of sample application region (Sample Pad)

In the present invention, the "sample pad" is a site serving as the sample application region receiving a sample, and any substances and forms are available as long as those in a state of being molded into a pad can absorb a liquid sample and allow passage of the liquid and the components of the analyte.

As described above, the sample pad of the present invention is pretreated with polyethylene glycol (PEG) having a molecular weight of 15,000 to 700,000.

The pretreatment of the sample pad with PEG may be applied to at least the sample application region where the sample is applied in the sample pad, may more widely be applied in the development direction than the sample application region, and is desirably applied to the entire sample pad. In other words, the sample application region is a sample dropping region and corresponds to a portion in contact with a sample dropping hole of the housing when the immunochromatographic test strip is stored in the housing to form a device.

The sample pad of the present invention may contain an erythrocyte agglutinating agent. In this case, the agent may be contained in at least a portion of the sample pad or may be contained in the whole thereof.

Specific examples of materials suitable for the sample pad include, but not limited to, glass fiber, acrylic fiber, hydrophilic polyethylene material, dry paper, paper pulp, woven fabric, etc. Preferably, a glass fiber pad is used. The sample pad can also have a function of a conjugate pad described later. The sample pad can also contain a blocking reagent usually used as needed without departing from the object of the present invention and without affecting the reaction system.

(Conjugate)

In the conjugate of the present invention, a specific binding substance or a control substance binding to an analyte is immobilized on a label.

The label used in the present invention may be any label capable of constituting the conjugate through sensitization (immobilization) of the specific binding substance such as an antibody and capable of serving as the label in a method in which the label is brought into contact with a sample to detect an analyte (such as an antigen) in the sample, and examples thereof include colloidal gold particles, colloidal platinum particles, colored latex particles, and magnetic particles, among which colloidal gold and colored latex are desirable, and colloidal gold is more desirable. The particle diameter thereof may be adjusted such that a desired detection sensitivity of the analyte is obtained depending on each type and, for example, the particle diameter of the colloidal gold particles is preferably 20 to 100 nm, more preferably 30 to 100 nm, particularly preferably 60 nm.

In the conjugate of the present invention, a region not bound to the specific binding substance can be blocked with a blocking agent on a surface of colloidal gold etc.

Regarding the presence form of the conjugate, the conjugate may be present in a form present as the conjugate pad, i.e., in a state of being contained in a dedicated pad (conjugate pad) other than the sample pad, the third pad, and the porous membrane (type A), or may be present as a conjugate part in a portion of the sample pad (type B). Alternatively, the conjugate may be present as a separate detection reagent separately from the test strip so as to be mixed with the specimen (type C).

A typical example of the test strip having the conjugate in the presence form of the type A will hereinafter be described.

Figure 5:
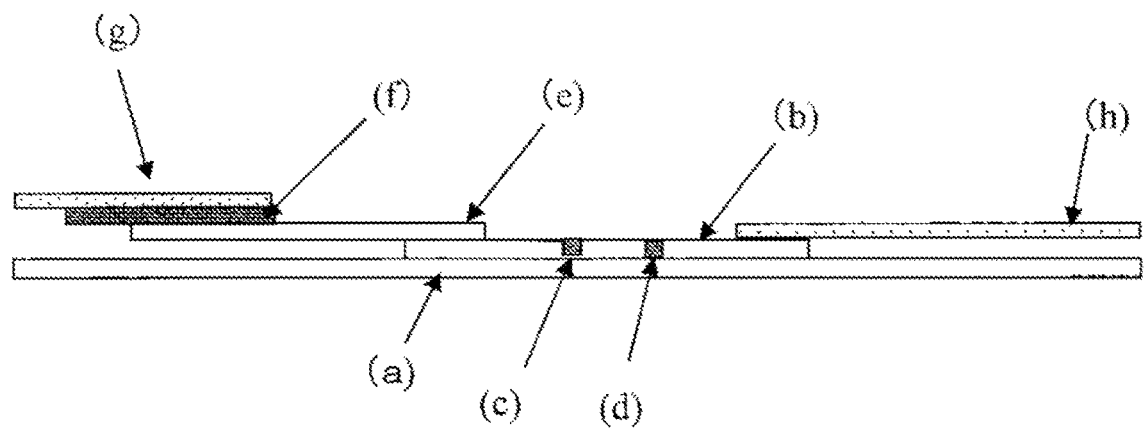
FIG. 5 is a schematic view showing an immunochromatographic test strip of the present invention.

The sample pad, the conjugate pad, the third pad, and the porous membrane are arranged in this order from upstream to downstream in the flow direction of the sample and are arranged such that upper and lower layers at least partially overlap with each other. A test strip of such an arrangement example is shown in FIG. 5.

When a sample containing an analyte is applied to the sample pad of such a test strip, the analyte flows through the sample pad to the conjugate pad on the downstream side. In the conjugate pad, the analyte and the conjugate come into contact with each other and pass through the pad while forming a complex. Subsequently, the complex passes through the third pad placed in contact with the lower surface of the conjugate pad and is developed into the porous membrane.

Since the porous membrane has the specific binding substance binding to an analyte immobilized on a portion thereof, the complex is bound and immobilized onto this membrane. The immobilized complex is detected by a means detecting absorbance, reflected light, fluorescence, magnetism, etc. derived from a labeling substance.

The test strip having the conjugate in the presence form of the type B will then be described.

A difference from the type A test strip is that the sample pad and the conjugate pad are integrated, i.e., that the sample application region and the conjugate part are formed in portions of the sample pad.

The sample application region is a site to which the sample containing an analyte is applied, while the conjugate part is a site containing the conjugate, and the sample application region is located upstream of the conjugate part.

The test strip having the conjugate in the presence form of the type C will then be described.

The difference from the type A test strip is that the conjugate pad is absent in the test strip and that the conjugate is present as a separate detection reagent (conjugate reagent). For example, a filter chip may be included that has the conjugate incorporated in a filter. By using such a filter chip to filter a specimen with the filter, the conjugate held in the filter and the analyte are combined to form a complex (aggregate). This complex can be applied to the same test strip as the type A except for the absence of the conjugate pad, so as to detect the analyte.

(Detection Reagent)

In the present invention, the "detection reagent" is specifically a solution containing at least a conjugate.

The detection reagent may contain, for example, one or more types of stabilizers, solubilizers, etc. for the purpose of maintaining the conjugate in a stable state so as to facilitate the specific reaction of the antibody immobilized on the conjugate with the analyte when mixed with the sample, or to quickly and effectively dissolve and fluidize the conjugate. Examples of the stabilizers, solubilizers, etc. can include bovine serum albumin (BSA), sucrose, casein, and amino acids.

The detection reagent may also contain known sensitizers and chelating agents such as EDTA and EGTA as needed for the purpose of improving the detection sensitivity.

In this description, the term "detection" or "measurement" must be construed in the broadest sense, including the existence proof and/or the quantitation of the analyte and must not be construed in a limited manner in any sense.

(Sample Diluent)

A diluent may be used in the present invention if dilution of a specimen is required depending on the concentration of an analyte in the specimen. The diluent having any composition may be used as long as the diluent does not significantly inhibit the reaction between the analyte and the specific binding substance or, conversely, does not significantly facilitate the reaction resulting in excessive aggregation of the label and causing a defect of development by capillarity, and does not make the signal detection of the reaction with the specific binding substance depending on the concentration of the analyte impossible.

(Conjugate Pad)

In the present invention, the "conjugate pad" refers to a pad acquired by impregnating a material suitable for the conjugate pad described later with a detection reagent that specifically reacts with the analyte and drying a material. The conjugate pad has a function of allowing the detection reagent and the analyte to form a complex when the sample passes through the conjugate pad. The conjugate pad itself may be placed in contact with a specific binding substance-immobilized membrane. Alternatively, the conjugate pad may be placed in contact with the sample pad so as to receive a specimen passing through the sample pad as a capillary flow and then transfer the specimen as a capillary flow to the 3rd pad in contact with a surface different from the contact surface for the sample pad. How to select one or more sites of the sample pad and the conjugate pad and how to arrange the selected sites on the specific binding substance-immobilized membrane can appropriately be changed.

Examples of materials suitable for the conjugate pad include, but not limited to, paper, cellulose mixture, nitrocellulose, polyester, acrylonitrile copolymer, glass fiber, and nonwoven fiber such as rayon. Preferably, a glass fiber pad is used.

The conjugate pad may contain a "control reagent" for securing reliability of detection results of an immunochromatographic detection method, for example, a specific binding substance labeled with a label and not reactive with a specimen component, and a highly antigenic protein such as KLH (keyhole limpet hemocyanin) labeled with a label, as needed. These control reagents are components (substances) considered as having no possibility of presence in the sample and can appropriately be selected.

(3rd Pad)

In the present invention, the 3rd pad can be placed between the sample pad and the insoluble membrane for the purpose of removing components unnecessary for detection of the analyte out of reactive components in the specimen and the detection reagent so that components necessary for reaction can smoothly be developed in the insoluble membrane on which the specific binding substance is immobilized. For example, it is desirable that blood cells, insoluble blood cell fractures, etc. are removed as the components unnecessary for detection. The 3rd pad may also be given an additional effect of preliminarily removing aggregates growing to a size preventing the movement to and the smooth development through the membrane on which the specific binding substance is immobilized, among the aggregates generated by the reaction between the analyte and the specific binding substance. The 3rd pad may be made of any material and in any form allowing the passage of liquid and a component to be detected as well as the detection reagent. Specific examples include, but not limited to, glass fiber, acrylic fiber, hydrophilic polyethylene material, dry paper, paper pulp, fabric, etc. The 3rd Pad may be referred to as a blood cell separation membrane when used for the purpose of separating blood cells. In the present invention, when whole blood is used as a specimen, the blood cell separation membrane is desirably used for certainly separating and removing blood cells not completely removed by the sample pad alone.

(Erythrocyte Agglutinating Agent)

In the present invention, when whole blood is used as a specimen, an erythrocyte agglutinating agent or an erythrocyte binding component is desirably used together in addition to the use of the 3rd Pad. Although the erythrocyte agglutinating agent or the erythrocyte binding component to be used together is not particularly limited, known examples thereof include lectin, a polyclonal antibody, and a monoclonal antibody, and a polycationic erythrocyte agglutinating agent is also usable. Examples of known polycationic erythrocyte agglutinating agents include polybrene, polylysine, polyacrylic amine, and polyalanine, and polybrene is preferable among them. Polybrene has a chemical name, hexadimethrine bromide, and is one of cationic polymers to which CAS No. 28728-55-4 is assigned.

The erythrocyte agglutinating agent or the erythrocyte binding component can be used in a form in which the agent or the component is added to a diluent for diluting a specimen or directly added to a specimen, or can be contained in the sample application region (sample pad) of the immunochromatographic test strip. In such a use form, erythrocytes in whole blood are agglutinated.

By using the PEG having a certain molecular weight of the present invention, the sample quickly permeates from the sample application region and is developed in the insoluble membrane. When the specimen is whole blood, elution of blood cell components into the membrane and clogging on the membrane tend to occur, and the use of the PEG of the present invention may promote these phenomena. However, the use of the 3rd Pad, the erythrocyte agglutinating agent, etc. effectively prevents the elution and clogging of blood cell components. Therefore, in the present invention, when whole blood is used as a specimen, by using the 3rd Pad, the hemagglutinin agent, etc. in addition to the use of the PEG having a certain molecular weight, an efficient immunochromatographic test strip can be provided in which the permeation of the whole blood specimen is quickly achieved without causing the elution and clogging of blood cell components.

(Immobilization of Specific Binding Substance on Insoluble Membrane)

The specific binding substance to the analyte can be immobilized on the insoluble membrane by a generally well-known method in the immunochromatographic test strip of the present invention. For example, in the case of the flow-through type, the specific binding substance is adjusted to a predetermined concentration, and a constant amount of the solution thereof is applied to the insoluble membrane in a specific symbol shape such as a dot or +. In this case, to ensure the reliability of the immunochromatographic detection method, a protein or compound capable of binding to the conjugate is typically immobilized at a position different from the specific binding substance to the analyte to form a "control detection region". The specific binding substance binding to the control reagent described above can be immobilized at a position different from the specific binding substance binding to the analyte to form a "control detection region".

In the case of the lateral-flow type, the specific binding substance is adjusted to a predetermined concentration, and the solution thereof is applied in a line shape to the insoluble membrane by using an apparatus etc. having a mechanism capable of moving a nozzle in a horizontal direction while discharging the solution at a constant rate therefrom. In this case, the concentration of the specific binding substance is preferably 0.1 to 5 mg/mL, more preferably 0.5 to 3 mg/mL.

An amount of the specific binding substance immobilized on the insoluble membrane can be optimized by adjusting an amount of application dropped onto the insoluble membrane in the case of the flow-through type, and can be optimized by adjusting a rate of discharge from the nozzle of the apparatus described above in the case of the lateral-flow type. Particularly, in the case of the lateral-flow type, 0.5 to 2 μL/cm is preferable. In the present invention, the term "flow through membrane assay" refers to a method in which a specimen solution etc. are developed to pass perpendicularly through the insoluble membrane, and the term "lateral flow membrane assay" refers to a method in which a specimen solution etc. are developed to move in a direction parallel to the insoluble membrane.

In the present invention, regarding the position of application of the specific binding substance binding to the analyte onto the insoluble membrane, in the case of the lateral-flow type, the position can be arranged such that the detection reagent is developed from the conjugate pad due to the capillarity and sequentially passes through lines to which respective specific binding substances are applied. Preferably, the line formed by applying the specific binding substance binding to the analyte is located upstream, and the line formed by applying the control specific binding substance is preferably located downstream thereof. In this case, the lines are desirably spaced at a sufficient distance so that the signal of the label can be detected. Even in the case of the flow-through type, the position of application of the specific binding substance binding to the analyte may be arranged so that the signal of the label can be detected.

The specific binding substance solution applied to the insoluble membrane can usually be prepared by using a predetermined buffer solution. Examples of the type of the buffer solution include commonly used buffer solutions such as phosphate buffer solution, Tris buffer solution, and Good's buffer solution. The pH of the buffer solution is preferably in a range of 6.0 to 9.5 and may appropriately be set depending on a property of the specific binding substance to be used. For example, a buffer solution having a pH of 8.0 can be used for an anti-cTnI specific binding substance described later. The buffer solution may further contain salts such as NaCl, stabilizers and preservatives such as sucrose, preservatives such as ProClin, etc. The salts include those contained for adjusting the ionic strength such as NaCl, and those added at the step of adjusting the pH of the buffer solution such as sodium hydroxide. After immobilizing the specific binding substance on the insoluble membrane, blocking can further be performed by coating an area other than the specific binding substance immobilization site with a normally used blocking agent turned into the form of solution or vapor. In this description, the insoluble membrane having the specific binding substance immobilized thereon as described above may be referred to as a "specific binding substance-immobilized membrane".

(Insoluble Membrane)

In the present invention, the insoluble membrane (hereinafter also simply referred to as a membrane) can be made of any material. Examples thereof include, but not limited to, polyethylene, polyethylene terephthalate, nylons, glass, polysaccharides such as cellulose and cellulose derivatives, or ceramics. Specific examples can include glass fiber filter paper and nitrocellulose membrane commercially available from Merck Millipore, Toyo Roshi Kaisha, GE Healthcare, etc. By appropriately selecting a pore size and a structure of the insoluble membrane, the rate at which the immune complex of the colloidal gold-labeled specific binding substance and the analyte flows through the membrane can be controlled. Since an amount of the labeled specific binding substance binding to the specific binding substance immobilized on the membrane can be adjusted by controlling the flow rate in the membrane, the pore size and the structure of the membrane are desirably optimized in consideration of combination with other constituent materials of the immunochromatographic test strip of the present invention.

(Absorption Pad)

In the present invention, the absorption pad is a site having liquid absorbability for controlling the development of the specimen by absorbing the specimen having moved and passed through the porous membrane. In the lateral-flow type, the absorption pad may be placed on the most downstream side of the test strip, and in the flow-through type, the absorption pad may be placed on a lower portion of the specific binding substance-immobilized membrane, for example. For the absorption pad, for example, filter paper can be used; however, the present invention is not limited thereto.

(Detection Device)

The immunochromatographic test strip of the present invention can be stored/mounted and used in a suitable container (housing) in consideration of the size of the test strip, the method and position of the addition of the specimen, the immobilization position of the specific binding substance on the specific binding substance-immobilized membrane, a signal detection method, etc., and the state of being stored/mounted in this way is referred to as a "device".

In the detection device of the present invention, in addition to the sample application region, a developing solution supply region for separately supplying a developing solution can be placed on the upstream side of the sample application region. By disposing the developing solution supply region and applying the developing solution, the development of the specimen applied from the sample application region can be promoted.

However, since the sample application region of the test strip of the present invention is pretreated with the certain PEG, the analyte can quickly be transferred to the development region and the detection region simply by applying the specimen from the sample application region, and therefore, even if the developing solution supply region is not placed in addition to the sample application region to promote the development of the specimen, the reaction can be allowed to progress to a certain extent within a predetermined time without individual difference of the immunochromatographic test strip, and variations in detection values can be suppressed.

Particularly, when whole blood is used as a specimen, a variation in development can effectively be suppressed. From the viewpoints of the complexity of performing application twice separately for the specimen and the developing solution and the simple structure, a device without the developing solution supply region is more desirable as the detection device of the present invention.

(Others)

In this description, the "insoluble membrane" may be represented as a "solid phase", and physically or chemically supporting an antigen or a specific binding substance with the insoluble membrane or the supporting state may be represented as "immobilizing", "immobilized", "solid phased", "sensitization", or "adsorption".

(Specimen)

In the detection method of the present invention, the "specimen" containing the analyte refers to a biological sample such as blood, urine, sputum, saliva, nasal discharge, nasal cavity swab, throat swab, other body fluids, and feces. The biological sample may directly be used as a specimen, and a sample appropriately diluted with a diluent or extracted and/or filtered is also included in the specimen of the present invention. Examples of blood specimens include whole blood, erythrocytes, plasma, serum, etc.

The blood specimen also includes a specimen collected by a blood collection tube to which an anticoagulant such as EDTA or heparin is added at the time of blood collection.

The present invention solves a problem of reduction in measurement value of a whole blood specimen as compared to that of a plasma specimen in immunochromatography and provides an effect of enabling an accurate measurement regardless of the type of specimen.

(Analyte)

The analyte of the present invention is a substance present in a biological specimen such as blood (whole blood), erythrocytes, serum, plasma, urine, saliva, or sputum and examples thereof include: inflammation-related markers such as CRP (C-reactive protein), IgA, IgG, and IgM; coagulation or fibrinolysis markers such as fibrin degradation products (e.g., D-dimer), soluble fibrin, TAT (thrombin-antithrombin complex), and PIC (plasmin-plasmin inhibitor complex); circulation-related markers such as oxidized LDL, BNP (brain natriuretic peptide), H-FABP (cardiac fatty acid-binding protein), and cardiac troponin I (cTnI); metabolism-related markers such as adiponectin; tumor markers such as CEA (carcinoembryonic antigen), AFP (α-fetoprotein), CA19-9, CA125, and PSA (prostate-specific antigen); infectious disease-related markers such as HBV (hepatitis B virus), HCV (hepatitis C virus), *Chlamydia* trachomatis, and gonococcus; allergen-specific IgE (immunoglobulin E), hormones, and drugs. Among these, D-dimer, CRP, BNP, H-FABP, cTnI, etc. associated with a high desire to use whole blood as a specimen are more preferable.

(Specific Binding Substance)

In the present invention, examples of the specific binding substance for an analyte substance supported by insoluble carrier particles such as colloidal gold include proteins, peptides, amino acids, lipids, sugars, DNA, RNA, receptors, and haptens, and although not particularly limited by the magnitude of molecular weight or the origin such as natural or synthetic, examples thereof include antibodies or antigens that may be used in immunological measurement methods utilizing an immune response.

(Antibody Used in the Present Invention)

The antibody to the analyte used in the present invention is not limited by a method of preparation as long as the antibody specifically reacts with the analyte, and may be a polyclonal antibody or a monoclonal antibody. More preferably, the antibody is a monoclonal antibody. In general, hybridomas producing the antibody can be prepared by cell fusion between the spleen cells of an animal immunized by using the analyte as an immunogen and the myeloma cells of the same species according to the method of Kohler and Milstein (see Nature, Vol. 256, p. 495 (1975)).

The antibody of the present invention can be a whole antibody molecule as well as a functional fragment of an antibody having an antigen-antibody reaction activity. The antibody may be an antibody obtained through an immunization step of general animals (mouse, goat, sheep, etc.), as well as an antibody having an amino acid sequence changed to that of an animal species different from the animal immunized with the immunogen (analyte) by a gene recombination technique, etc. (such as a chimera antibody, a humanized antibody, or a fully humanized antibody). Examples of the functional fragment of the antibody include F(ab')2 or Fab', which is a fragment having an antigen-antibody reaction activity, and a single-chain antibody (scFv). These functional fragments can be produced by treating the antibody obtained as described above with a proteolytic enzyme (e.g., pepsin or papain).

In a relationship between an antibody for immobilization on a label (first antibody) and an antibody for immobilization on an insoluble membrane (second antibody) when the antibodies used in the measurement method for detecting an analyte through so-called sandwich formation are monoclonal antibodies, the epitope of the second antibody used is different from that of the first antibody when the epitope of the first antibody is monovalent, and the epitope of the second antibody used may be the same as or different from that of the first antibody when the epitope of the first antibody is polyvalent.

(Kit)

A detection kit utilizing the immunochromatographic detection method of the present invention may be a kit that includes an immunochromatographic test strip including at least a porous membrane and having a sample application region, a development region, and a detection region on which a specific binding substance is immobilized, and the immunochromatographic test strip is characterized by being treated with PEG having a certain molecular weight.

The detection kit may include another reagent required for detection (e.g., a detection reagent containing a conjugate), a specimen diluent, a test tube, a filtration filter, a cotton swab for specimen collection, an instruction manual, a housing for storing the test strip, etc.

Specific examples of the present invention will hereinafter be described; however, these are for illustrative purposes only, and the present invention is not limited thereto.

EXAMPLES

[Example 1] CV Reduction Effect of Sample Pad of the Present Invention in Plasma Specimen 1. Fabrication of Detection Device of the Present Invention
   1) Preparation of Colloidal Gold-Labeled Anti-cTnI Monoclonal Antibody (Anti-cTnI Antibody Conjugate)
   (i) Preparation of Colloidal Gold Solution To 500 mL of purified water heated to 93° C., 1 mL of a 7% (w/v) triammonium citrate aqueous solution was added and mixed by stirring. Subsequently, 1 mL of a 5% (w/v) tetrachloroauric(III) acid aqueous solution was added and reacted for 10 minutes with stirring, and the reaction solution was then boiled. Subsequently, the solution was cooled in ice water to prepare a solution of colloidal gold having an average particle diameter of 60 nm. This solution of colloidal gold having an average particle diameter of 60 nm was adjusted with purified water to an absorbance of 1 OD/mL at the maximum absorption wavelength of colloidal gold.

(ii) Preparation of Anti-cTnI Antibody Conjugate

To the 1 OD/mL colloidal gold solution (pH 8.0), an anti-cTnI monoclonal antibody diluted to 20 µg/mL with a 2 mM Tris-hydrochloric acid buffer solution (pH 7.0) was added and stirred for 10 minutes at room temperature. To the mixture liquid of the colloidal gold and the antibody, purified water containing 0.5% (w/v) of Neo Protein Saver (Toyobo, No. NPS-301) was added and stirred for 5 minutes at room temperature. Subsequently, the mixture was centrifuged at 11900×g for 45 minutes at 10° C. After removing a supernatant, 1 mL of a 0.2% (w/v) Neo Protein Saver aqueous solution was added to an obtained sediment to suspend a conjugate to obtain an anti-cTnI antibody conjugate.

(iii) Preparation of Colloidal Gold-Labeled KLH (KLH Conjugate) for Control Line To 20 mL of the 1 OD/mL colloidal gold solution, 10 mL of KLH (prepared by Sigma) dissolved in a 2 mmol/L phosphate buffer solution to 620 µg/mL was added and stirred for 10 minutes at room temperature. To the mixture liquid of the colloidal gold and KLH, 1 mL of a 10% bovine serum albumin (BSA) aqueous solution was added and stirred for 5 minutes at room temperature. Subsequently, the mixture was centrifuged at 10° C. for 45 minutes, and after removing a supernatant, 1 mL of conjugate diluent was added to an obtained sediment to suspend a conjugate to obtain a KLH conjugate.

2) Fabrication of Conjugate Pad

A conjugate solution was prepared by mixing the anti-cTnI antibody conjugate at 3 OD, the KLH conjugate at 0.75 OD, 0.5% LipidureBL-1301, 0.25 mg/ml Heteroblock, 2.4% lactose, 2.0% NPS, and 20 mM MOPS (pH 7.2), and a glass fiber pad (Merck Millipore) having a certain volume is impregnated with a 1.2-fold amount of the solution relative to the volume of the pad. The pad was dried by heating in a dry oven at 70° C. for 45 minutes to obtain a conjugate pad.

3) Fabrication of Anti-cTnI Monoclonal Antibody-Immobilized Membrane (Antibody-Immobilized Membrane)

For a test line, a solution was prepared by adding sucrose and an anti-cTnI monoclonal antibody to 10 mM PB pH 8.0 containing 0.09% NaN$_3$ to the final concentration of 2.5% and 3 mg/mL.

For a control line, a rabbit anti-KLH polyclonal antibody (prepared by Bethyl) was diluted and prepared as described above.

At a position inside one end of a short side of a nitrocellulose membrane (Hi-Flow plus HF180, Merck Millipore), the anti-cTnI monoclonal antibody was set to 1 μL/cm and applied in a line shape perpendicular to the longitudinal direction of the test strip (the development direction) by using the immunochromatographic dispenser "XYZ3050" (BIO DOT) to form the test line. The anti-KLH polyclonal antibody was similarly applied at an interval of about 4 mm from the position of the test line to form the control line. The membrane was dried at 70° C. for 45 minutes in a dry oven to obtain an antibody-immobilized membrane.

4) Fabrication of Sample Pad: A glass fiber pad (Lydall) was cut to a size of 16 mm×6 mm, impregnated with a sample pad pretreatment solution described below in a volume of 60.5 μL, and dried in a dry oven at 70° C. for 45 minutes, and was used as a sample pad.

(i) Sample Pad Pretreatment Solution of the Present Invention

A sample pad pretreatment solution of the present invention was obtained by adjusting 20 mM MOPS (pH 7.2) containing 20 mM MOPS (pH 7.2) containing 0.5% glucose, 2% polybrene, and 0.25% PEG20K (retaining amount per sample pad area is 0.158 mg/cm$^2$).

PEG2K, PEG6K, and PEG20K used in the examples including the following test examples were prepared by Kishida Chemical Co., Ltd., and PEG70K and PEG500K were prepared by FUJIFILM Wako Pure Chemical Corporation.

(ii) Sample Pad Pretreatment Solution of Comparative Example

A sample pad pretreatment solution of Comparative Example was obtained by preparing 20 mM MOPS (pH 7.2) containing 0.5% glucose and 2% polybrene.

5) Fabrication of Immunochromatographic Test Strip

The antibody-immobilized porous membrane was affixed to a plastic adhesive sheet (a), application parts are arranged such that the anti-cTnI antibody (c) on the upstream side of the development is followed by the anti-KLH antibody (d), and the blood cell separation membrane (3rd pad) (e) was further mounted on the membrane.

Subsequently, the conjugate pad (f) fabricated in 2) was arranged and mounted; the sample pad (g) fabricated in 4) was arranged and mounted to overlap the conjugate pad; and the absorption pad (h) was arranged and mounted at an end on the opposite side. By cutting a structure having the constituent elements overlapped with each other in this way, an immunochromatographic test strip was fabricated. The test strip may be stored in/mounted on a special plastic housing (having a sample addition window part and a detection window part, not shown in FIG. 5) in the form of a detection device at the time of an assay. FIG. 5 shows a schematic configuration diagram of the immunochromatographic test strip.

2. Measurement by Immunochromatography

To the sample addition window part of the detection device fabricated as described above, 120 μL of a plasma specimen solution containing 700 pg/mL cardiac troponin I (cTnI) was added, and the color development amount (absorbance) of the test line was measured 15 minutes later by using the immunochromatographic reader, Rapid Pia (registered trademark, Sekisui Medical Co., Ltd.) to calculate each of CV values (variations) thereof. CV denotes Coefficient of Variation and can be obtained by dividing the standard deviation by the mean value. The results are shown in FIG. 1

3. Results

When the troponin of the plasma specimen was measured with the immunochromatographic test strip including the sample pad pretreated with 0.25% PEG20K, the CV value was suppressed, and the measurement reproducibility was improved, as compared to the case of the sample pad pretreated with a solution containing no PEG.

Figure 2:
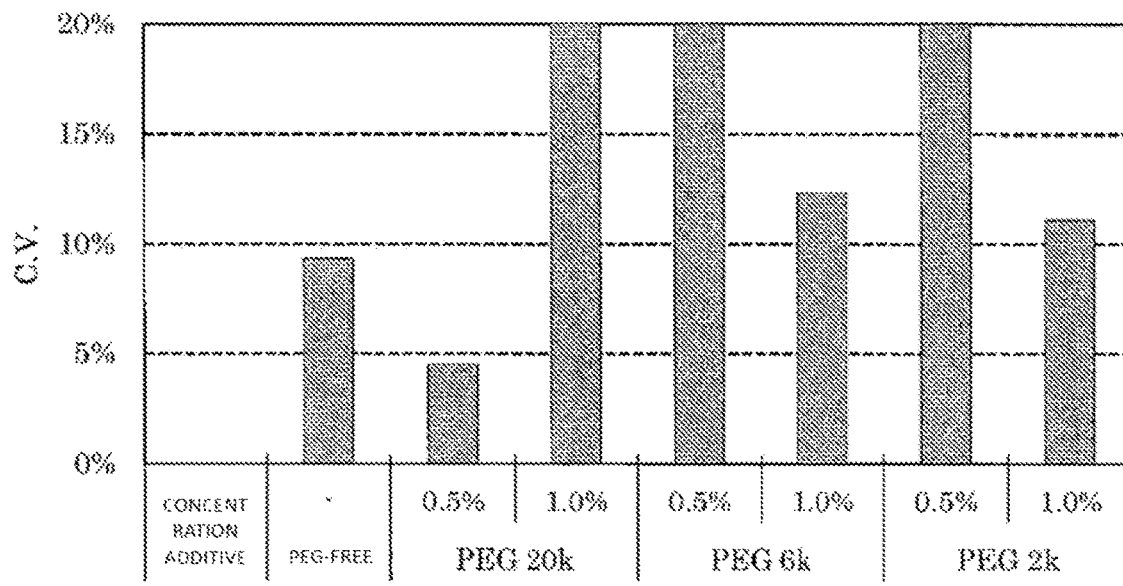
FIG. 2 is a graph showing variations in measurement values when the molecular weight and concentration of PEG contained in the sample pad are changed. PEG is 20K, 6K, or 2K, and the concentration is 0.5%, or 1.0%.

[Example 2] Relationship Between PEG Molecular Weight (Low Molecular Weight Side) and CV Reduction Effect While PEG20K was used for the pretreatment of the sample pad in Example 1, PEG6K (molecular weight 6,000) and 2K (molecular weight 2,000) were also tested to examine a relationship between PEG on the low molecular weight side and the CV reduction effect. The concentrations of PEG pretreatment were 0.5% and 1.0% in each test. Except this, the tests were performed as in Example 1. The results are shown in FIG. 2.

According to the results, only PEG20K had the CV value reduction effect as compared to the case of the pretreatment with a PEG-free solution, and no CV reduction effect was observed for PEG6K and PEG2K even though the concentration was increased to 1%.

[Example 3] Relationship Between PEG Molecular Weight (High Molecular Weight Side) and CV Reduction Effect The effect was confirmed on the high molecular weight side of PEG. Specifically, while PEG20K was used for the pretreatment of the sample pad in Example 1, PEG70K and 500K were also tested to examine the relationship between PEG on the high molecular weight side and the CV reduction effect. The specimen was a plasma specimen solution containing 300 pg/mL cardiac troponin I (cTnI), and the concentration of PEG pretreatment was 0.25%. Except this, the tests were performed as in Example 1. The results are shown in Table 1.

According to the results, it was found that the CV reduction effect on the high molecular weight side is equal to or higher in both cases than PEG20K, which is already confirmed to have the effect.

TABLE 1

|  | Molecular weight PEG concentration | PEG 20k 0.25% | PEG 70k 0.25% | PEG 500k 0.25% |
| --- | --- | --- | --- | --- |
| Measurement value (mAbs) | 1 | 90.2 | 97.8 | 90.1 |
|  | 2 | 96.5 | 89.5 | 89.4 |
|  | 3 | 88.3 | 99.6 | 85.4 |
|  | 4 | 86.8 | 94.3 | 94.4 |
|  | 5 | 87.6 | 93.0 | 93.3 |
|  | Avg. | 89.9 | 94.8 | 90.5 |
|  | S.D. | 3.91 | 4.00 | 3.55 |
|  | C.V. | 4.3% | 4.2% | 3.9% |

[Example 4] Relationship Between PEG Sample Pad Retaining Amount and CV Reduction Effect The effect was confirmed in terms of the retaining amount of PEG20K in the sample pad. Specifically, while a 0.25% solution of PEG20K was used for the pretreatment of the sample pad in Example 1, 0.5% (a retaining amount per sample pad area was 0.315 mg/cm$^2$) and 0.75% (the amount was 0.473 mg/cm$^2$) were also tested to examine a relationship between the retaining amount of PEG and the CV reduction effect. The specimen was a plasma specimen solution containing 60 pg/mL of cardiac troponin I (cTnI), and except this, the tests were performed as in Example 1. The results are shown in Table 2.

Figure 6:
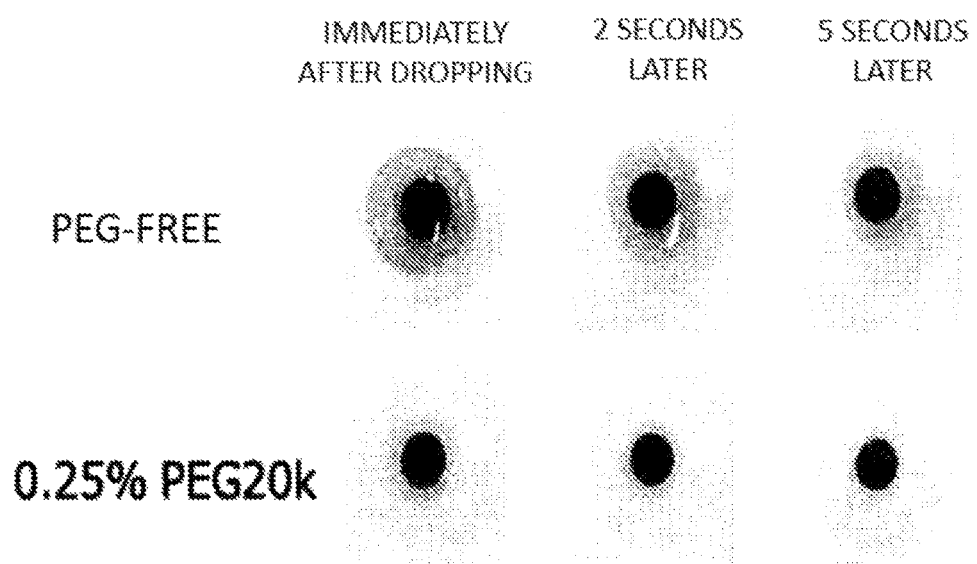
FIG. 6 is a photograph showing states of permeation immediately, 2 seconds, and 5 seconds after a specimen solution was dropped onto the sample pad (PEG-free and 0.25% PEG20K-pretreated sample pads).

Additionally, a degree of permeation into the pad was visually compared and observed immediately, 2 seconds, and 5 seconds after dropping the specimen solution onto the sample pad by using the PEG-free and PEG20K 0.25% pretreated sample pads. The observation result is shown in FIG. 6 as a photograph.

According to the result, it was found that the CV reduction effect is provided in all the retaining amount ranges. It was also confirmed that the specimen solution quickly permeated the test strip.

TABLE 2

|  |  | PEG-FREE | PEG 20k 0.25% | PEG20k 0.5% | PEG 20k 0.75% |
|---|---|---|---|---|---|
| Measurement value (mAbs) | 1 | 16.8 | 21.1 | 23.8 | 38.5 |
|  | 2 | 20.8 | 20.1 | 25.0 | 39.3 |
|  | 3 | 28.0 | 22.1 | 25.6 | 42.5 |
|  | 4 | 23.4 | 19.1 | 29.0 | 40.9 |
|  | 5 | 15.7 | 19.9 | 30.2 | 40.3 |
|  | 6 | 19.3 | 19.6 | 31.7 | 41.6 |
|  | 7 | 16.6 | 19.6 | 27.1 | 37.9 |
|  | 8 | 18.5 | 18.4 | 27.6 | 41.8 |
|  | 9 | 17.3 | 21.4 | 28.4 | 38.5 |
|  | Avg. | 19.6 | 20.2 | 27.6 | 40.1 |
|  | S.D. | 3.95 | 1.18 | 2.53 | 1.66 |
|  | C.V. | 20.2% | 5.9% | 9.2% | 4.1% |

[Example 5] CV Reduction Effect of the Sample Pad of the Present Invention on Whole Blood Specimen A test was conducted to check whether the same effect was obtained when the specimen was changed from a plasma specimen to whole blood. For the specimens, three types of whole blood specimens (hematocrit value: 20%, 39%, 54%) containing 300 pg/mL cTnI were used. The pretreatment of the sample pad was performed as in Example 1 except that PEG20K having a concentration of 0.15% was used.

Figure 3:
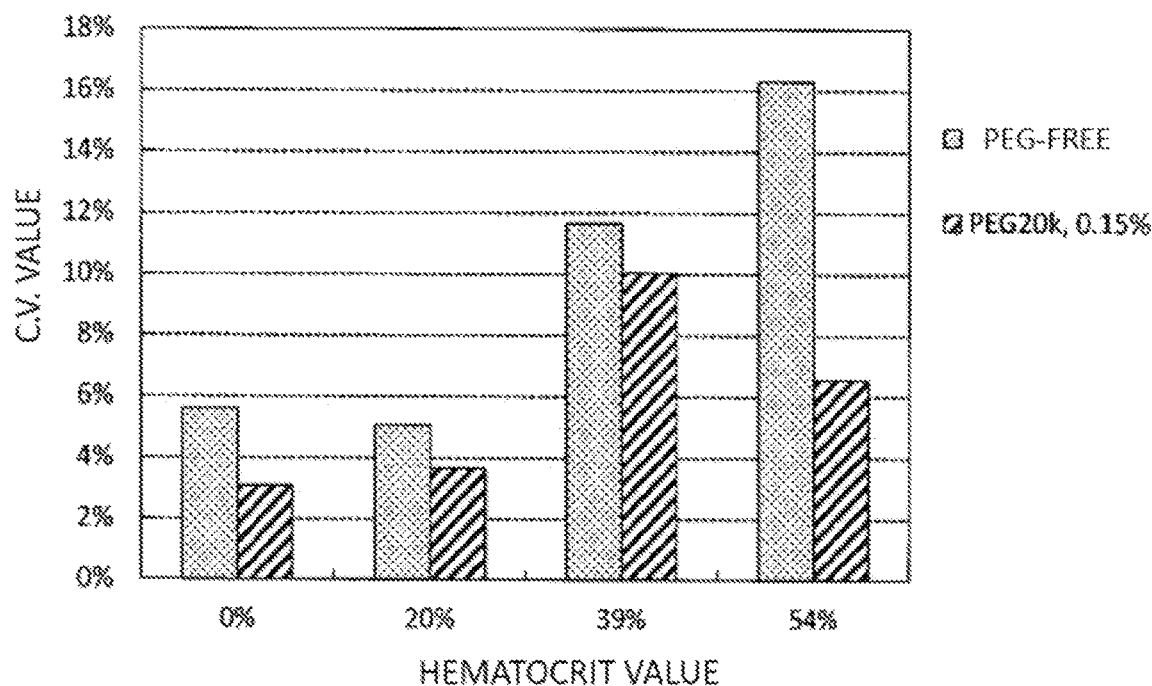
FIG. 3 is a graph showing variations in measurement values when the specimen is whole blood in the cases of sample pads containing PEG (the present invention) and not containing PEG (Comparative Example). Whole blood with a hematocrit value of 0 (i.e., plasma), 20, 39, or 54% was used.

For reference, the same test was performed on a specimen with a hematocrit value of 0% (plasma). The results are shown in FIG. 3.

According to the results, the effect of the present invention was confirmed for the whole blood specimens having any of the hematocrit values. Specifically, the CV value was improved in all the whole blood specimens having the hematocrit values of 20%, 39%, and 54% by pretreating the sample pad with 0.15% PEG20K. Particularly, even in the case of a highly viscous specimen having a hematocrit value of 54%, quick penetration into the membrane was achieved.

[Example 6] Relationship Between PEG Molecular Weight (High Molecular Weight Side) and CV Reduction Effect in Whole Blood Specimen The effect was also confirmed on the high molecular weight side of PEG. Specifically, the specimen of Example 3 was replaced with a whole blood specimen solution having a hematocrit value of 55% containing 300 pg/mL of cardiac troponin I (cTnI), and the same tests were performed. The results are shown in Table 3.

According to this result, it was found that the CV reduction effect on the high molecular weight side is much higher in both cases than PEG20K, which is already confirmed to have the effect.

Therefore, it was found that the variations in measurement values in the immunochromatographic detection method are improved by pretreating the sample pad with the PEG having a certain molecular weight of the present invention.

TABLE 3

|  |  | Molecular weight PEG concentration | PEG 20k 0.25% | PEG 70k 0.25% | PEG 500k 0.25% |
|---|---|---|---|---|---|
| Measurement value (mAbs) | 1 |  | 77.3 | 71.7 | 74.4 |
|  | 2 |  | 71.2 | 66.4 | 77.3 |
|  | 3 |  | 69.8 | 64.5 | 80.7 |
|  | 4 |  | 64.0 | 64.9 | 79.4 |
|  | 5 |  | 63.2 | 68.7 | 75.6 |
|  | Avg. |  | 69.1 | 67.2 | 77.5 |
|  | S.D. |  | 5.76 | 2.97 | 2.60 |
|  | C.V. |  | 8.3% | 4.4% | 3.4% |

Figure 4:
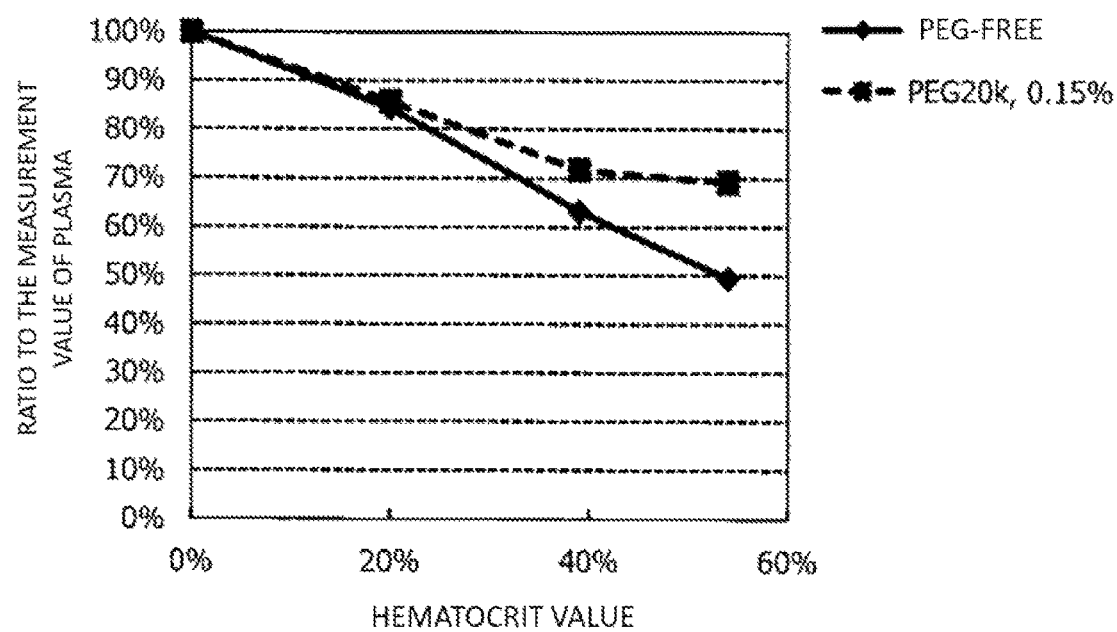
FIG. 4 is a graph showing a ratio of the measurement value of whole blood having each hematocrit value in the case that the measurement value is 100 when the specimen is plasma.

[Example 6] Relationship Between Sensitivity Ratio of Whole Blood Measurement Value to Plasma Measurement Value and Hematocrit Value For the whole blood measurement value obtained in Example 5, a ratio to the measurement value of plasma (with a hematocrit value of 0%) was calculated to examine a relationship between the hematocrit value and the measurement sensitivity. The calculation result is shown in FIG. 4

According to this figure, it was found that when the pretreatment of the sample pad of the present invention is not performed, the sensitivity obtained in the whole blood specimen relatively decreases as the hematocrit value increases as compared to the sensitivity obtained in the plasma specimen, while the decrease in sensitivity can be suppressed by performing the pretreatment of the present invention. Therefore, it was found that even when whole blood is measured, the variations in measurement values can be suppressed and the measurement can sensitively be performed.

INDUSTRIAL APPLICABILITY

According to the present invention, by containing certain polyethylene glycol in the sample application region of the immunochromatographic test strip, a specimen can be allowed to quickly permeate the test strip in the sample application region, and the immunochromatographic test strip causing less variations in measurement values can be provided. Particularly, the immunochromatographic test strip causing less variations in measurement values can be provided regardless of the type of the specimen.

REFERENCE SIGNS LIST (a) plastic adhesive sheet
(b) antibody-immobilized membrane
(c) anti-cTnI antibody (test line)
(d) anti-KLH antibody (control line)
(e) blood cell separation membrane (3rd pad)
(f) conjugate pad (g) sample pad (h) absorption pad

The invention claimed is:

1. An immunochromatographic test strip configured to receive a whole blood specimen comprising at least a sample application region, a development region, and a detection region, wherein the sample application region is pretreated with polyethylene glycol (PEG) having a molecular weight of 15,000 to 700,000,
  wherein the sample application region further contains an erythrocyte agglutinating agent or an erythrocyte binding component adapted to prevent the elution and clogging of blood cell components,
  wherein the content of the polyethylene glycol per area of the sample application region is 0.00630 to 0.473 mg/cm$^2$,
  wherein the immunochromatographic test strip comprises a sample pad as the sample application region, and
  wherein the sample pad is made of glass fiber.

2. The immunochromatographic test strip according to claim 1,
  wherein the test strip comprises a conjugate pad,
  wherein a labeled specific binding substance that binds to an analyte is retained in a dissolvable state in the conjugate pad, and
  wherein the conjugate pad serves as a portion of development region.

3. The immunochromatographic test strip according to claim 1, wherein a blood cell separation membrane is placed between the sample pad and the detection region.

4. The immunochromatographic test strip according to claim 1, wherein the erythrocyte agglutinating agent is polybrene, polylysine, polyacrylic amine, or polyalanine.

5. An immunochromatographic detection kit comprising: the immunochromatographic test strip according to claim 1.

6. The immunochromatographic test strip according to claim 1, wherein the erythrocyte binding component is lectin, a polyclonal antibody, of a monoclonal antibody.

7. An immunochromatographic test strip comprising at least:
  (a) a sample pad made of glass fiber containing polyethylene glycol having a molecular weight of 15,000 to 700,000;
  (b) a conjugate pad in which a first specific binding substance binding to an analyte and labeled with colloidal gold is held in a dissolvable state; and
  (c) a membrane on which a second specific binding substance binding to an analyte is immobilized, wherein the membrane is a porous membrane,
  wherein the sample pad further contains an erythrocyte agglutinating agent or an erythrocyte binding component adapted to prevent the elution and clogging of blood cell components,
  wherein the content of the polyethylene glycol per area of the sample application region is 0.00630 to 0.473 mg/cm$^2$.

8. The immunochromatographic test strip according to claim 7,
  wherein the test strips comprises a blood cell separation membrane, and
  wherein the sample pad, the conjugate pad, the blood cell separation membrane, and the porous membrane are arranged in this order from upstream to downstream in the flow direction of the sample.

9. The immunochromatographic test strip according to claim 7, wherein the conjugate pad is made of glass fiber.

10. The immunochromatographic test strip according to claim 7, wherein the erythrocyte binding component is lectin, a polyclonal antibody, or a monoclonal antibody.

11. The immunochromatographic test strip according to claim 7, wherein the erythrocyte agglutinating agent is polybrene, polylysine, polyacrylic amine, or polyalanine.

12. A method for producing an immunochromatographic test strip comprising at least a sample application region, a development region, and a detection region, the method comprising:
  impregnating the sample application region with a solution or a plurality of solutions containing: polyethylene glycol having a molecular weight of 15,000 to 700,000; and an erythrocyte agglutinating agent or an erythrocyte binding component adapted to prevent the elution and clogging of blood cell components, and
  drying the sample application region,
  wherein concentration of the polyethylene glycol of the solution is adjusted so that a retaining amount of the polyethylene glycol per area of the sample pad is 0.00630 to 0.473 mg/cm$^2$.

13. The method for producing an immunochromatographic test strip according to claim 12, wherein the immunochromatographic test strip comprises a sample pad as the sample application region.

14. The method according to claim 12, wherein the erythrocyte binding component is lectin, a polyclonal antibody, or a monoclonal antibody.

15. The method according to claim 12, wherein the erythrocyte agglutinating agent is polybrene, polylysine, polyacrylic amine, or polyalanine.

* * * * *